US012765784B2

(12) United States Patent
Osiroff et al.

(10) Patent No.: US 12,765,784 B2
(45) Date of Patent: Oct. 20, 2026

(54) FACIAL INTERFACE HAVING INTEGRATED HEALTH SENSORS

(71) Applicant: Apple Inc., Cupertino, CA (US)

(72) Inventors: Nadav Osiroff, Tel Aviv (IL); Oriel Y. Bergig, Shoham, CA (US); Javier Mendez, San Jose, CA (US); Raviv Erlich, Rehovot (IL); Boris Gendelsman, Tel Mond (IL)

(73) Assignee: APPLE INC., Cupertino, CA (US)

( * ) Notice: Subject to any disclaimer, the term of this patent is extended or adjusted under 35 U.S.C. 154(b) by 329 days.

(21) Appl. No.: 18/460,275

(22) Filed: Sep. 1, 2023

(65) Prior Publication Data

US 2024/0090777 A1 Mar. 21, 2024

Related U.S. Application Data

(60) Provisional application No. 63/376,428, filed on Sep. 20, 2022.

(51) Int. Cl.

| | |
|---|---|
| ***A61B 5/0205*** | (2006.01) |
| ***A61B 5/00*** | (2006.01) |
| ***A61B 5/024*** | (2006.01) |
| ***A61B 5/08*** | (2006.01) |

(52) U.S. Cl.

CPC .......... *A61B 5/0205* (2013.01); *A61B 5/6803* (2013.01); *A61B 5/742* (2013.01); *A61B 5/02438* (2013.01); *A61B 5/0816* (2013.01); *A61B 2562/0247* (2013.01); *A61B 2562/028* (2013.01)

(58) Field of Classification Search

CPC ..... A61B 5/0205; A61B 5/6803; A61B 5/742; A61B 5/02438; A61B 5/0816; A61B 2562/0247; A61B 2562/028

See application file for complete search history.

(56) References Cited

U.S. PATENT DOCUMENTS

| | | | | |
|---|---|---|---|---|
| 11,402,640 | B1 * | 8/2022 | Singamsetty | G02B 7/008 |
| 2011/0107838 | A1 * | 5/2011 | Suijlen | G01L 9/0019 73/702 |
| 2017/0273599 | A1 * | 9/2017 | Reese | G01L 1/142 |
| 2018/0348863 | A1 * | 12/2018 | Aimone | G06F 3/016 |
| 2019/0250651 | A1 * | 8/2019 | Liu | G05D 16/2066 |
| 2021/0271091 | A1 * | 9/2021 | Xu | G02B 27/017 |

* cited by examiner

*Primary Examiner* — Amanda L Steinberg

(74) *Attorney, Agent, or Firm* — Dorsey & Whitney LLP

(57) ABSTRACT

A head-mountable device can include a display, a facial interface attached to the display to contact a face of a user, and a sensor unit attached to the facial interface. The sensor unit can include a deformable pad that contacts a nasal region of the user, a channel defining an internal volume, and a pressure sensor in fluid communication with the deformable pad through the internal volume.

20 Claims, 6 Drawing Sheets

FACIAL INTERFACE HAVING INTEGRATED HEALTH SENSORS

CROSS-REFERENCE TO RELATED APPLICATION(S)

This claims priority to U.S. Provisional Patent Application No. 63/376,428, filed 20 Sep. 2022, and entitled "Facial Interface Having Integrated Health Sensors," the entire disclosure of which is hereby incorporated by reference.

FIELD

The described embodiments relate generally to a facial interface of a head-mountable device. More particularly, the present embodiments relate to a facial interface of a head-mountable device including a pressure sensor assembly for detecting biometric information from a user.

BACKGROUND

Recent advances in portable computing have enabled head-mountable devices (HMD(s)) that provide augmented and virtual reality (AR/VR) experiences to users. The ever increasing complexity and functionality of these head-mountable devices encourages constant improvements to the electrical components and sensors of the HMD.

Sensors can be utilized on head-mountable devices for various purposes, such as detecting user information, biometric information, user identity, movement, location, environmental detection, health evaluations, performance evaluations, etc. An arrangement of sensors that are suitably integrated into the limited surfaces area and which comply with the material, structural and intended function of the sensor and head-mountable device is needed.

Sensors in conventional head-mountable devices are employed in rudimentary ways, if at all, creating a limited user experience, and leading to user dissatisfaction and user discomfort. Indeed, sensors in conventional head-mountable devices can contribute to bulky, heavy, and/or cumbersome devices, whose sensors are ineffective at achieving their full potential.

SUMMARY

According to some aspects of the present disclosure, a head-mountable device can include a display, a facial interface attached to the display to contact a face of a user, and a sensor unit attached to the facial interface. The sensor unit can include a deformable pad that contacts a nasal region of the user, a channel defining an internal volume, and a pressure sensor in fluid communication with the deformable pad through the internal volume.

In some examples, the channel fluidically connects the deformable pad and the pressure sensor. The internal volume can include an internal pressure. The deformable pad can deflect in response to a movement of the face. The internal pressure of the channel can change in response to the deflection. The pressure sensor can detect the change in the internal pressure.

In some examples, the pressure sensor is disposed within the facial interface. The sensor unit can be a first sensor unit, the head-mountable device can include a second sensor unit positioned to contact a forehead of the user when the head-mountable device is worn. The sensor unit can detect a pulse of the user. The sensor unit can detect a respiration of the user. The sensor unit can detect a facial expression of the user.

In some examples, the facial interface is a first facial interface, the first facial interface can be interchangeable with a second facial interface on the head-mountable device. The sensor unit can be a first sensor unit, wherein the second facial interface includes a second sensor unit, different than the first sensor unit.

According to some aspects, a facial interface for a wearable device can include a housing defining an internal volume, a pressure sensor positioned in the internal volume, and a membrane moves in response to facial movements. The membrane can include a first surface to contact a face of a user when the facial interface is being worn, and a second surface in fluid communication with the pressure sensor. The membrane can be positionally adjustable relative to the housing. The pressure sensor can transmit an output to cause a change in the wearable device.

In some examples, the membrane is a deformable elastomer. A pressure in the internal volume can change based on movement of the membrane, the change in pressure being detectable by the pressure sensor. A stiffness of the membrane can be adjustable. The pressure sensor can have a sensitivity of about 2.5 millibar.

According to some aspects, a wearable electronic device includes a display, a facial interface positioned between the display and a face of a user when the wearable electronic device is worn by the user, an inflatable member to deform in response to facial movements, and a pressure sensor. The pressure sensor can detect a deformation in the inflatable member, and transmit a signal to a processor, the signal being based on the deformation in the inflatable member.

In some examples, the sensor and the inflatable member are in fluid communication. The sensor can include a pressure-based micro-electro mechanical system (MEMS) sensor. The facial interface can define a channel that fluidically couples the sensor and the inflatable member. The inflatable member can removably couple to the facial interface, forming a sealed connection. The processor can cause the wearable electronic device to perform an action based on the signal.

BRIEF DESCRIPTION OF THE DRAWINGS

The disclosure will be readily understood by the following detailed description in conjunction with the accompanying drawings, wherein like reference numerals designate like structural elements, and in which.

DETAILED DESCRIPTION

Figure 1:
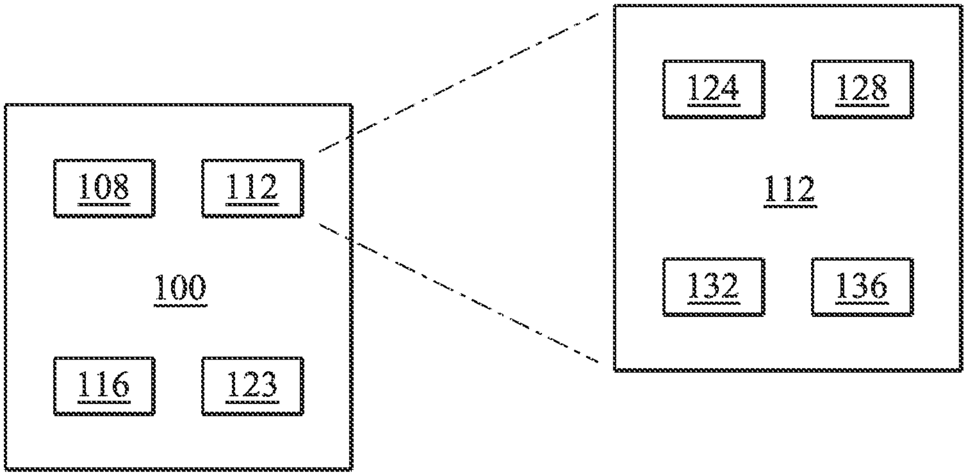
FIG. 1 shows a block diagram of a head-mountable device.

The following detailed description makes detailed reference to representative embodiments illustrated in the accompanying drawings. The following descriptions are not intended to limit the examples to one preferred embodiment. Rather, they are intended to cover alternatives, modifications, and equivalents as can be included within the spirit and scope of the described embodiments, as defined by the appended claims.

The following disclosure relates to a facial interface of a head-mountable device. More particularly, the present embodiments relate to a facial interface of a head-mountable device including a pressure sensor assembly used for acquiring biometric information. It will be understood the head-mountable device (HMD) in the present disclosure can apply to AR/VR head sets and also to smart computer glasses. In some examples, a processor causes a component of the HMD to perform an action in response to the biometric information collected by the sensor(s). As used herein "an action" or "perform an action" can refer to any electrical or mechanical act causing a change in one or more of the components of the HMD. For example, an action can include displaying a notification for the user and/or activating or deactivating one or more components.

In some examples, a sensor can collect biometric information from the nose and/or forehead of the user wearing the device, including when they are performing an activity, like exercising. The biometric information can be related to pulse, respiration, facial expression, heart rate, blood pressure, changes in the cartilage, chewing, or any other pertinent data. In some examples, a combination of sensors (sensor fusion) can be used to determine the biometric information. For example, a facial expression can be determined using both the pressure-based MEMS sensor described herein as well as an internal facing camera of the HMD. Further, in response to the collected data, the system can perform an action, for example, notifying the user of the collected data.

Head-mountable devices equipped with sensors are utilized for various purposes that detect user feedback, such as positioning or movement feedback, providing limited information in response to a user. For example, a user may have an increase in respiration or heart rate while performing a movement or action. Conventional head-mountable devices are not appropriately equipped to capture all the desired biometric information.

In contrast, the head-mountable devices of the present disclosure include a facial interface that can be incorporated or integrated with sensor(s), such as a pressure sensor assembly, configured to collect user data, such as biometric information, including pulse, respiration, facial expressions, heart rate, blood pressure, etc. By capturing the user data, the pressure sensor assembly of the facial interface can provide increased and improved feedback to the user. A head-mountable device with sensors monitoring user biometrics or health feedback creates a highly customized user experience, unlike the sensors of a conventional head-mountable device, which are unable to consider the user experience to such a degree.

Pressure sensor assemblies positioned on the facial interface can be used to create a customized user experience. The head-mountable device of the present disclosure can include pressure sensors to measure a user's response or engagement via indicators, such as pulse, respiration, facial expressions, heart rate, blood pressure, etc. Additionally, the sensor data can be used to monitor user fatigue, facial expressions, change in a user state, or obtain activity-specific metrics.

The head-mountable device can include sensors that are integrated on/in the facial interface in a variety of different ways. For example, the head-mountable device of the present disclosure can implement a first facial interface with a first sensor assembly being interchangeable, along with a second facial interface with a second sensor assembly. In some examples, the removably attached sensor assembly can correspond to a different user activity, such as exercise, health, clinical settings, learnings activities, etc.

These and other embodiments are discussed below with reference to FIGS. 1-6. However, those skilled in the art will readily appreciate that the detailed description given herein with respect to these Figures is for explanatory purposes only and should not be construed as limiting. Furthermore, as used herein, a system, a method, an article, a component, a feature, or a sub-feature comprising at least one of a first option, a second option, or a third option should be understood as referring to a system, a method, an article, a component, a feature, or a sub-feature that can include one of each listed option (e.g., only one of the first option, only one of the second option, or only one of the third option), multiple of a single listed option (e.g., two or more of the first option), two options simultaneously (e.g., one of the first option and one of the second option), or combination thereof (e.g., two of the first option and one of the second option).

FIG. 1 illustrates a block diagram of a head-mountable device 100 including a frame or housing 116, a display 108, a facial interface 112, and a support 123. The display 108 can include one or more optical lenses or display screens in front of the eyes of a user. The display 108 can include a screen or display unit for presenting an augmented reality visualization, a virtual reality visualization, or other suitable visualization to a user. Additionally, the display 108 can be positioned in or on the housing 116. Similarly, a facial interface 112 can be connected to the housing 116. In some examples, the housing 116 can support or house a variety of electronic components, including the display 108.

The facial interface 112 can include one or more sensors (e.g., pressure sensors) 124, support attachments 132, display attachments 128, and feedback or output modules 136. The sensors 124 can be removably attached to the facial interface 112. As used herein, the terms "facial interface," "engagement interface," or "light seal" refer to a portion of the head mountable device 100 that engages (i.e., contacts or conforms to) a user's face.

In particular, the facial interface 112 can include portions of a head-mountable device that conform to, or press against, regions of a user's face. The facial interface 112 can be positioned between the display 108 or frame 116 and the user's face. In some examples, the facial interface 112 can include a pliant (or semi-pliant) facetrack or lumen that spans the forehead, wraps around the eyes, contacts other regions of the face (etc., zygoma and maxilla regions), and bridges the nose.

In addition, the facial interface 112 can include various components forming a frame, structure, housing, or webbing of the head mountable device 100 disposed between the display 108 and the user's skin. In some examples, the facial interface 112 can include a seal (e.g., a light seal, environment seal, dust seal, air seal, etc.). As used herein, the term "seal" can include partial seals or inhibitors, in addition to complete seals (e.g., a partial light seal where come ambient light is blocked and a complete light seal where all ambient light is blocked when the head-mountable device 100 is donned). The facial interface 112 can be removably attached to the housing 116 and can be in electrical communication with the display 108.

The sensor(s) 124 of the facial interface 112 can collect biometric information, such as the user's vital sign (including pulse data, respiration data, and blood pressure). The pressure sensor assembly 124 can generate a signal based on the collected user information and transmit the signal to a processor that can cause an output 136 to perform an action in response to the signal (i.e., in response to the biometric information collected). For example, a user can perform a rigorous activity, such as lifting weights or working out while wearing the HMD 100. During such activity, the user's heart rate or other vital signs can elevate or change, being detectable by the sensor 124.

The sensor 124 can generate one or more signals based on the received input. The sensor 124 can transmit the signal to one or more components of the HMD 100 (e.g., to the display 108 and/or the output 136). The display 108, being in electrical communication with the facial interface 112, can receive electrical communication and provide feedback to the user related to their biometric readings (e.g., visual feedback, audio feedback, haptic feedback, etc.). Feedback can include determining when a user needs to take a break, or when the difficulty of an activity needs to be lowered or raised, the output 136 can include scheduling various activities for the user or recommending adjustment of the HMD 100.

As used herein, the term "sensor," "sensors," "pressure sensor assembly," or "sensor assembly" can refer to one or more sensing devices, such as a MEMS pressure sensor. In some examples, the HMD 100 includes a pressure sensing assembly having a deformable pad that deflects in response to a movement of a user's face, creating an increase or decrease in internal pressure of a pressure channel (e.g., a fluid volume connecting a deformable pad and a pressure sensors in fluid communication with the deformable pad) that changes in response to the deflection. The change in internal pressure caused by a movement in the user's face can be detected by a pressure sensor connected fluidly connected to the channel and attached to the deformable pad.

In some examples, the sensor is capable of detecting a deflection of the deformable pad as small as 10 microns. In some examples, the sensor is capable of detecting a deflection of the deformable pad that is less than as 10 microns. In some examples, the sensor is capable of detecting a deflection of the deformable pad as small as 20 microns. In some examples, the sensor is capable of detecting a deflection of the deformable pad as small as 50 microns. In some examples, the sensor is capable of detecting a deflection of the deformable pad as small as 100 microns. In some examples, the sensor is capable of detecting a deflection of the deformable pad greater than 100 microns. In some examples, the sensor is capable of detecting a deflection of the deformable pad that is approximately 100 nanometers or less.

The term "pressure sensor" or "sensor" used within the context of this application can refer to a sensor capable of sensing pressure, such as a compact based microphone (e.g., a MEMS sensor) with a sensitivity of about 2.5 millibar. In some examples, the pressure-based MEMS sensor can have a sensitivity of about 250 Pascal. In some examples, the pressure-based MEMS sensor can include an electrical circuit, such as a Winston bridge, to detect nano-metric deflections of the deformable pad. A pressure sensor or a sensor used for this application can be sensitive enough to detect a pulse, respiration, or other pressure related feedback related to a user.

In some instances, the change in pressure detected in a pressure sensor or sensor can generate an electrical signal capable of being interpreted by a controller/processor as a facial expression. In some examples, the pressure assembly is tuned to capture a specific pressure range applicable to a certain activity requiring other sensitivity values including approximately 1 millibar, 1.5 millibar, 3 millibar, or 4.5 millibar. When the pressure sensor is paired with another pressure sensor, a rate can be captured, such as blood volume, pulse rate, or other rates applicable and interpretable from the cardiovascular system.

In some examples, certain sensors can be used to assess stress and emotion through changes in pressures via direct contact with a user's face. The HMD can then provide feedback or output related to the detected stress and emotion. In some examples, the sensors can operate through coin cell battery or Bluetooth connectivity. In some examples, the sensors are powered by a primary battery of the HMD.

The sensors described herein can allow for observations of the cardiovascular system and respiration, to observe relaxation and stress indicators, mental health, medical treatments, etc. Using the disclosed sensors integrated on the facial interface, physicians and care takers could have live feedback of biometrics. Use cases can include fitness settings, user content, workplace, telepresence, clinical, education, training, pain, therapy, etc. In some examples, the sensors can be used to capture facial expressions. This is particularly relevant given the user's face is covered by the HMD when worn. For example, the HMD could include a micro electro-mechanical system (MEMS) to detect changes in blood vessel diameter, blood pressure, pulse, heat rate, respiration, and detecting facial expressions.

Any of the features, components, and/or parts, including the arrangements and configurations thereof shown in FIG. 1 can be included, either alone or in any combination, in any of the other examples of devices, features, components, and parts shown in the other figures described herein. Likewise, any of the features, components, and/or parts, including the arrangements and configurations thereof shown and described with reference to the other figures can be included, either alone or in any combination, in the example of the devices, features, components, and parts shown in FIG. 1.

Figure 2A:
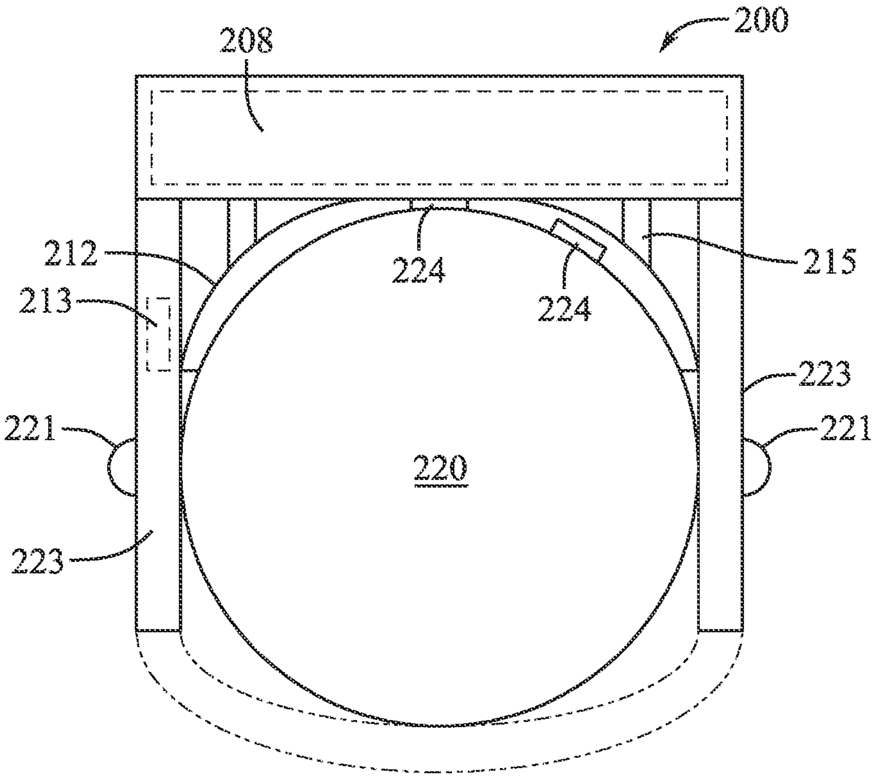
FIG. 2A shows a top view of an example head-mountable device.

FIG. 2A illustrates a head-mountable device 200. The head-mountable device 200 can be substantially similar to, including some or all of the features of, the head-mountable devices described herein, such as head-mountable device 100. In some examples, the head-mountable device 200 includes a controller 213 (e.g., sensor controller). While the controller 213 is illustrated as being positioned in the support (e.g. support arm) 223, the position of the controller 213 is not limited to the support 223, but can be positioned in/on the facial interface 212 or in the HMD display housing.

The controller 213 can include a processor and a memory device storing computer-executable instructions that, when executed by the processor, cause the controller to receive biometric data from one or more pressure sensor assemblies 224, transmit a signal based on the sensor data, and generate a signal to cause a component to perform an action in response to the received signal.

The controller 213 can include one or more processors (e.g., a system on chip, integrated circuit, driver, microcontroller, application processor, crossover processor, etc.). Further, the controller 213 can include one or more memory devices (e.g., individual nonvolatile memory, processor-embedded nonvolatile memory, random access memory, memory integrated circuits, DRAM chips, stacked memory modules, storage devices, memory partitions, etc.). In certain implementations, the controller 213 is communicatively coupled to a power source (e.g., a battery).

In some examples, the controller 213 stores sensor data received from the sensor assembly 224 in the memory. The controller 213 can receive and/or transmit signals based on sensor data. For example, as will be described below, the controller 213, by way of the processor and memory, can transmit a signal to the display 208 based on the sensor data from the pressure sensor (e.g., causing the display 208 or the head-mountable device 200 to perform an action, such as present a certain message, power off, react to biometric feedback, etc.).

The controller 213 can perform any number of different functions. For example, the memory device can store computer-executable instructions that, when executed by the processor, cause the controller to receive sensor data from the sensor assemblies 224 and transmit a signal based on the sensor data. For instance, the controller 213 can transmit a sensor signal to a display 208.

In response to the controller 213 the display 208 can perform a wide variety of actions, including power off or power on, react to a user generated facial expression, present a digital notification (e.g., user-generated notification, push notification, context-generated notification, system-generated notification, smart notification, etc.). In some examples, the memory device can store computer-executable instructions that, when executed by the processor, cause the controller 213 to receive biometric data from the sensor assemblies 224, transmit a signal based on the sensor data, and perform an action in response to the signal.

As illustrated, the head-mountable device (e.g., wearable electronic device) 200 can include the display 208, the facial interface 212, and the pressure sensor(s) 224 coupled to the facial interface 212. The pressure sensor assembly 224 can be embedded, encapsulated, deposited, adhered, or otherwise attached to the facial interface 212. A portion of the pressure sensor assembly 224, such as a deformable pad configured to contact a user's face, can deflect in response to a movement of a user's face.

The pressure sensor assembly 224 can be configured to detect a biometric feature of the user 220. The pressure sensor assembly 224, upon detecting a signal from the biometric feature, can transmit the signal to a component of the head-mountable device 200 causing the head-mountable device 200 to perform an action. For example, the head-mountable device 200 can change shape (i.e., tighten or loosen), move, vibrate, rotate, recalibrate, or reposition in response to the sensor signal of the biometric feature.

The head-mountable device 200 can include a headband, a retention band, a strap, or a support 223 connected to the display 208 and/or the frame 216. The support 223 can secure the display 108 and/or housing 216 relative to the user's head 220 (e.g., such that the display 208 is maintained in front of a user's eyes). The support 223 can be constructed from elastic material, inelastic material, or a combination of elastic and inelastic material.

The support 223 can be adjustable such that the support 223 conforms to the various shapes and sizes of a user's head 220. In some examples, the support 223 secures the head-mountable device 200 via friction between the user's head 220 and the retention band 223. In some examples, the support 223 elastically secures the head-mountable device 200 to the user's head 220. In some examples, the support 223 is coupled to a ratchet system or mechanism securing the head-mountable device 200 to the user's head 220. In some examples, the support 223 is disposed above or on an ear 221 of the user 220, supporting the head-mountable device 200.

In some examples, the housing or frame 216 of the head-mountable device 200 is connected via a connector 215 to the facial interface 212, the retention band 223 being connected to the frame 216 and/or the facial interface 212, securing the head-mountable device 200 to the user's head 220 above or over the ears 221 of the user.

Figure 2B:
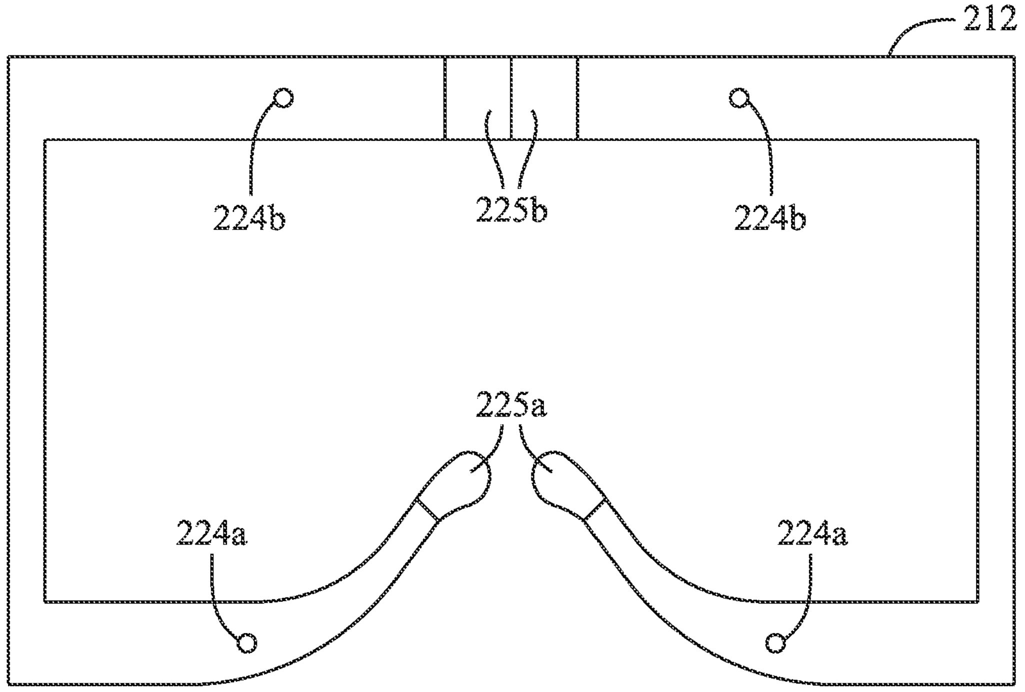
FIG. 2B shows a rear view of an example facial interface for a head-mountable device.

FIG. 2B shows an example facial interface 212 including one or more deformable pads 225*a* and 225*b* (collectively referred to as "deformable pads 225") disposed on the facial interface 212. The deformable pads 225 can include thin membranes or sheets. The deformable pads 225 can be inflatable membranes or pillows. While multiple deformable pads 225 are shown, it will be understood that one deformable pad 225 and sensor 224 can be used to achieve the same or similar results. The deformable pads 225 can be in fluid communication with one or more pressure sensors 224*a* and 224*b* (collectively referred to as "pressure sensors 224").

It will be noted that because of the use of deformable pad 225, the pressure sensors 224 do not need to be in direct contact with the user's skin. This allows the sensors 225 to be more securely housed within the facial interface 212 where motion on the user's skin can be transferred through various materials of the facial interface 212 to the deformable pad 225. The deformable pads 225 can be located at any location of the facial interface 212 that enables them to contact a face of a user. In some examples, the deformable pads 225*a* are located at/on a nose of a user when the head-mountable device is worn. The deformable pads 225*a* can be in fluid communication with the pressure sensors 224*a*. The pressure sensors 224*a* can detect changes in pressure caused by a movement in the deformable pads 225*a*.

The movement in the deformable pads 225*a* can be caused by a movement of the user's face. For example, a user may breathe through his/her nose, deflecting the deformable pads 225*a*, and thereby a change in internal pressure of the pressure sensor assembly. The pressure sensors 224 can detect the change in pressure and transmit a signal based on the change to the head-mountable device, such as the head-mountable device 200 shown in FIG. 2A, via an electrical signal. In some examples the change in pressure results in a piezoelectric reaction, a change in resistance, or a diaphragm deflection to generate the signal.

Similarly, the deformable pads 225*b* can be located near a forehead region of a user's face when the facial interface 212 is donned. The deformable pads 225*b* can be in fluid communication with the pressure sensors 224*b*. The pressure sensors 224*b* can detect changes in pressure caused by a movement in the deformable pads 225*b* in response to a movement of a user's face. For example, a user may perform an activity, such as making a facial expression or exercising, increasing the user's blood pressure, and thereby causing the detectable forehead vasculature to enlarge.

As the forehead vasculature enlarges, deformable pads 225*b* deflect, causing a change in internal pressure to the pressure assembly. The pressure sensors 224*b* detects the change in pressure and communicates the pressure change by generating an electrical signal in response to the pressure change, which signal can then be transmitted to the head-mountable device. Likewise, a change in the user's facial expression can cause a deflection of the deformable pads 225*b* which can be detected by the pressure sensors 224*b*. The pressure sensors 224*b* then generate an electrical signal in response to the detected deflection, which signal can then be analyzed by a processor to infer a characteristic of the user's facial expression.

Any of the features, components, and/or parts, including the arrangements and configurations thereof shown in FIGS. 2A-2B can be included, either alone or in any combination, in any of the other examples of devices, features, components, and parts shown in the other figures described herein. Likewise, any of the features, components, and/or parts, including the arrangements and configurations thereof shown and described with reference to the other figures can be included, either alone or in any combination, in the example of the devices, features, components, and parts shown in FIGS. 2A-2B.

Figure 3:
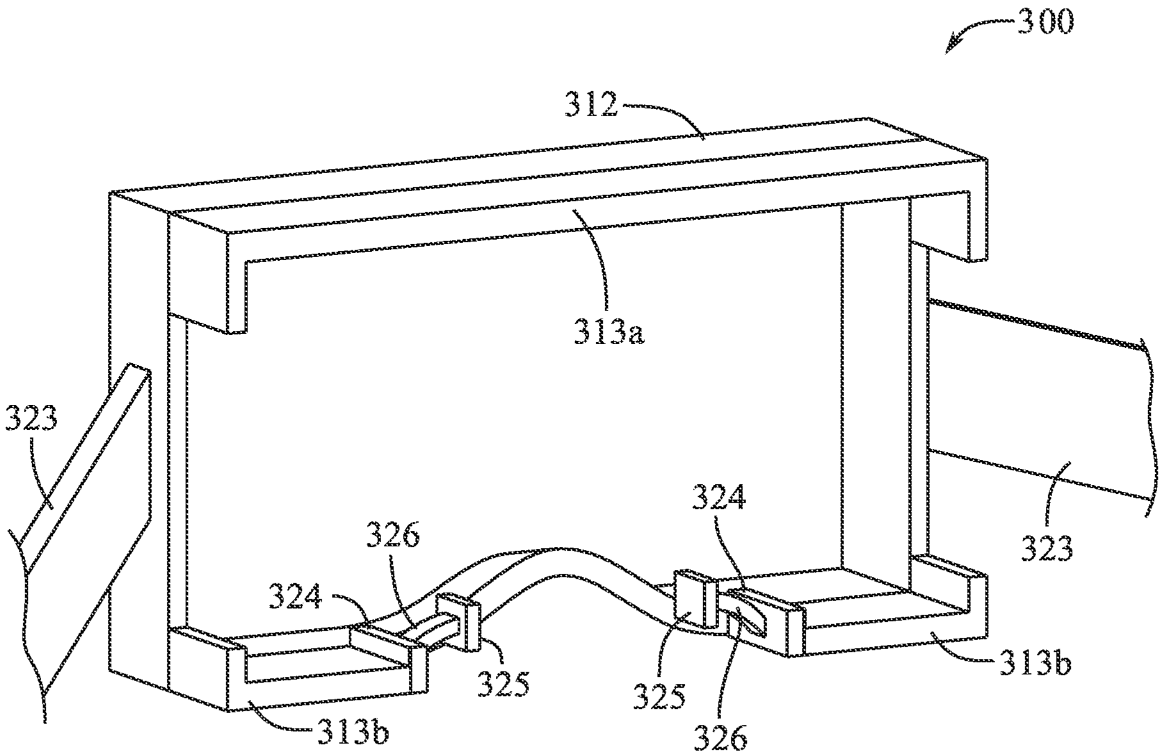
FIG. 3 shows a rear perspective view of a facial interface with sensors disposed near a nasal region of a head-mountable device.

FIG. 3 shows a rear perspective view of a head-mountable device 300. The head-mountable device 300 can be substantially similar to, and can include some or all of the features of, the head-mountable devices described herein, such as head-mountable device 100 and 200. The head-mountable device 300 shown in FIG. 3 includes a support 323, a facial interface 312, overmolded portions 313*a* and 313*b* (collectively referred to as "overmolded portion 313") connected to the facial interface 312, deformable pads 325, channels 326, and sensors 324.

The channel 326 allows for fluid communication between the deformable pad 325 and the sensor 324. As described in further detail with regards to FIGS. 4A and 4B, the channel 326 can define an internal volume. In some examples, the channel 326 defines a support arm for the deformable pad 325. The channel 326 can be adjustable such that the position of the deformable pad 325 relative to the user's nose can be modified for varied applications or users. For example, one user may have specific nose shape, and another user may have a substantially different nose shape. The channel 326 can be adjusted, such that the nose shape can be accommodated in a comfortable and precise manner.

In some examples, the deformable pads 325 can be adjustable. For example, the deformable pads 325 can move or pivot relative to the facial interface 312. The deformable pads 325 can change their pitch, yaw, or roll in order to establish a better fit and comfort on the user's face. In some examples, the stiffness or rigidity of the deformable pads 325 can be adjusted or tuned based on needs and preferences. The stiffness of the deformable pads 325 can be adjusted based on the pressure in the channels 326. In some examples, the deformable pads 325 are automatically adjusted based on the user or application. Further details regarding deformable pads are provided below with reference to FIGS. 4A and 4B.

In some examples, a user may perform a rigorous activity, requiring more rigid contact of the deformable pad 325. The deformable pad 325 can be replaced with a more rigid deformable pad. In some examples, the deformable pad 325 can be replaced with a less rigid deformable pad to accommodate other certain activities, such as test taking or learning activities.

The overmolded portion 313 can include portions contacting the user's face. For example, overmolded portion 313*b* can contact the maxilla and/or zygoma facial regions, creating a comfortable conforming fit to a user's face. Similarly, the overmolded portion 313*a* can contact a user's forehead conforming to each user's forehead unique attributes, providing a comfortable customized fit for an individual user. In some examples, the overmolded portion 313 can be considered part of the facial interface 312. The overmolded portions 313 can secure the sensor assembly to the facial interface 312, creating an esthetically pleasing head-mountable display. In some examples, the overmolded portions 313 can create or define the channels 326. In some examples, the overmolded portions 313 can form a housing to house or conceal the sensors 324 and/or channels 326.

Any of the features, components, and/or parts, including the arrangements and configurations thereof shown in FIG. 3 can be included, either alone or in any combination, in any of the other examples of devices, features, components, and parts shown in the other figures described herein. Likewise, any of the features, components, and/or parts, including the arrangements and configurations thereof shown and described with reference to the other figures can be included, either alone or in any combination, in the example of the devices, features, components, and parts shown in FIG. 3.

Figure 4A:
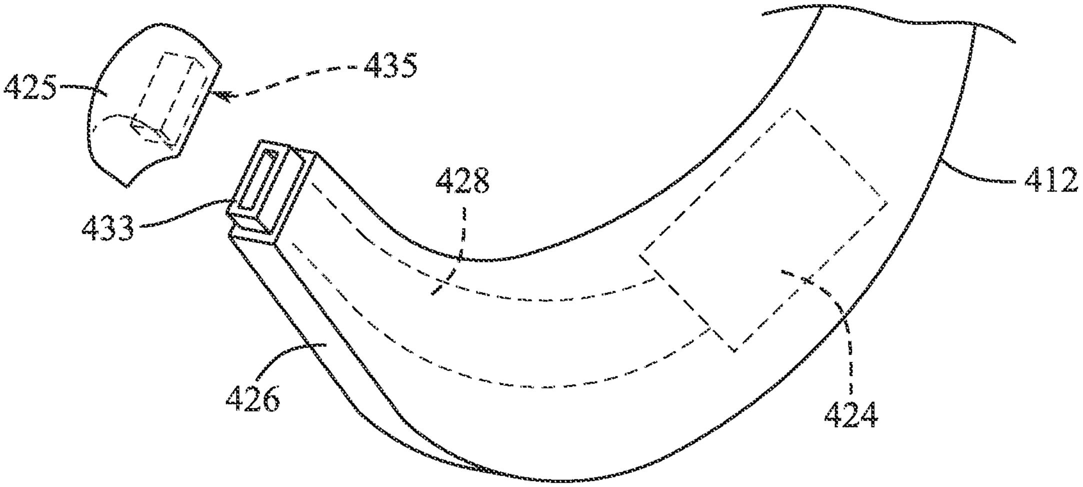
FIG. 4A shows an exploded perspective view of pressure sensor assembly of a head-mountable device.

FIG. 4A shows a perspective view of a portion of a facial interface 412. The facial interface 412 can be substantially similar to, and can include some or all of the features of, the facial interfaces described herein, such as facial interfaces 112, 212, and 312. The facial interface 412 can include an arm or channel 426 that defines an internal volume 428. The internal volume 428 can establish a fluid communication between a deformable pad 425 and a sensor 424. In some examples, the internal volume includes air or some other gas. In some examples, the internal volume 428 include a liquid or pneumatic fluid. The sensor 424 can be a pressure-based MEMS sensor 424. The sensor 424 can be disposed within the arm 426 of the facial interface 412. In some examples, the sensor 424 is positioned on an exterior of the arm 426.

The deformable pad 425 can include an inflatable member that can flex or deform in response to an external force. The deformable pad 425 can be removably attached to the arm 426 via a connector 433. The connector 433 can any suitable mechanical or magnetic attachment mechanisms. In some examples, the connector 433 can include a barbed configuration capable of removably securing the deformable pad 425 to the arm 426. The deformable pad 425 can include a female connector 435 to receive a male connector 433 on the arm 426. In some examples, the connector 433 can be threaded such that the deformable pad 425 is threaded onto the connector 433.

The term "barbed" used within the context of this application can define one end of a component connecting to another end of a different component. For example, the deformable pad can connect to the facial interface 412 via a barbed connection. The connection can be physical and contain egressed portions on one component and ingress portions on another components. These egressed portions and ingress portions can form a threaded fit, snap fit, compressive fit, or other fit that can produce fluid communication between the deformable pad 425 and the sensor 424.

Figure 4B:
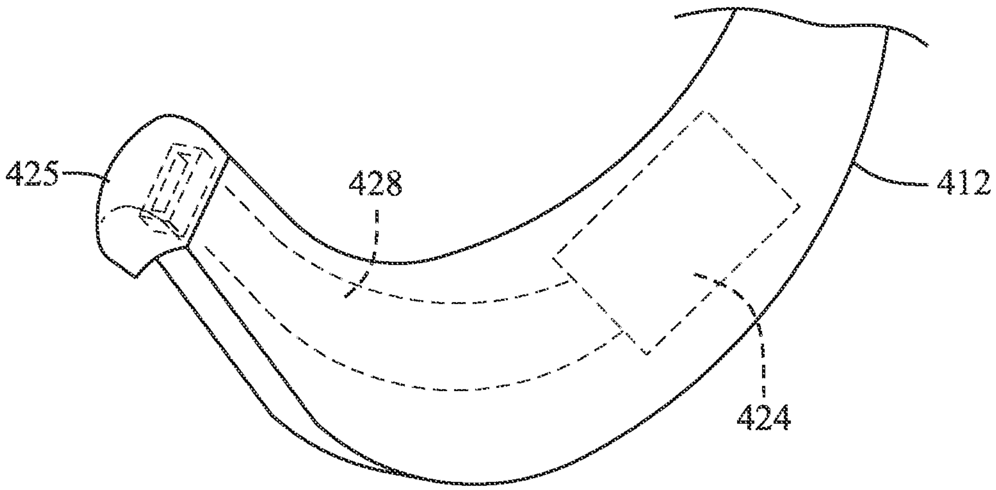
FIG. 4B shows an assembled perspective view of a pressure sensor assembly of a head-mountable device.

As shown in FIG. 4B, in some examples the connector 433 can establish a substantially air-tight seal between the deformable pad 425 and the internal volume 428 of the channel. In some examples, the gasket, O-ring, or other type of seal is positioned around the connector 433 to improve the seal. In some examples, a known and predetermined amount of air is permitted to escape the internal volume 428 as the deformable pad 425 moves. By controlling the amount of escaped air, the pressure sensor is still able to deduce facial movement.

The deformable pad 425 can be include an elastomeric material. The deformable pad 425 can include a soft material that is comfortable on the user's skin. The deformable pad 425 can include, but is not limited to, any of the following: Natural Rubber, Polyisoprene, Butyl Rubber (IIR, Isobutene-isoprene), Chloroprene (CR, Neoprene®), Ethylene Propylene Diene (EPDM), Fluorocarbon (FMK, Viton®), Fluorosilicone (FSI), Nitrile Butadiene (NBR), Saturated Nitrile (HNBR), Silicone Rubber (SI, Gum and Liquid), Styrene Butadiene (SBR), and Urethane (PU, Polyurethane).

In some examples, the deformable pad can include a compressible elastomer such as a silicon material that is durable and not likely to wear down. The deformable pad can be soft and resilient to moisture, such as sweat. In some examples, the deformable pad is overmolded or can be a stand-alone piece that is attached to the facial interface.

Further, the deformable pad 425 can be tuned for specific needs or users. For example, one deformable pad can be constructed of one elastomeric material for one application or user, and another deformable pad can include elastomeric material designed for another application or user. In some examples, the deformable pad 425 can be shaped or manufactured to increase or decrease sensitivity of the deformable pad 425 for a certain activity. In some examples, the deformable pad 425 can be constructed of a combination of materials, such as two or more types of elastomeric materials.

An example operation of the sensor module can occur when a user, wearing the HMD, has facial movement. A facial movement can include movement in the nose, forehead, cheeks, or any other portion of the face/head. Facial movements can be indicative of respiration, pulse, and facial expressions. Because the deformable pad 425 is in close proximity or touching the user, the facial movement can push or deflect the deformable pad 425 a certain amount. The deflection of the deformable pad 425 can cause a temporary increase in the pressure within the channel 426. The change in pressure can be detected by the sensor 424, which transmits a signal, based on the pressure fluctuation to be processed (e.g., by a processor on board the HMD). In some examples, the sensor 424 can be integrated into other components of the HMD (e.g., integrated onto the headband of the HMD).

Any of the features, components, and/or parts, including the arrangements and configurations thereof shown in FIGS. 4A-4B can be included, either alone or in any combination, in any of the other examples of devices, features, components, and parts shown in the other figures described herein. Likewise, any of the features, components, and/or parts, including the arrangements and configurations thereof shown and described with reference to the other figures can be included, either alone or in any combination, in the example of the devices, features, components, and parts shown in FIGS. 4A-4B.

Figure 5A:
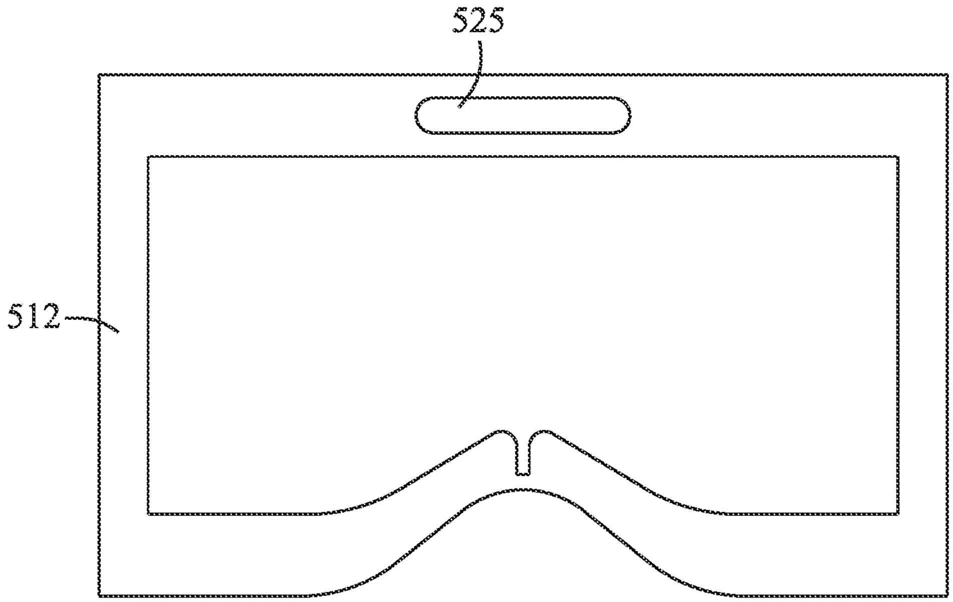
FIG. 5A shows sensors disposed on a forehead region of a facial interface of a head-mountable device.

FIG. 5A shows a rear view of a facial interface 512. The facial interface 512 can be substantially similar to, and can include some or all of the features of, the facial interfaces described herein, such as facial interfaces 112, 212, 312, and 412. In some examples, the facial interface 512 can include a pressure sensor located in a forehead-contacting region of the facial interface 512. The pressure sensor can include a deformable pad (e.g., inflatable member) 525. In some examples, the deformable pad is overmolded to the facial interface 512, sealing the deformable pad 525 and creating a pressure chamber wherein facial movements of a user cause the deformable pad 525 to deflect or deform. The deflection of the deformable pad 525 creates a change in pressure within the pressure chamber. The change in pressure can be detectible to the pressure sensor which can then generate a signal to be analyzed or interpreted by a processor/controller.

As illustrated in FIG. 5A, the deformable pad 525 can include an elongated shape. The elongated shape of the deformable pad 525 can span across a substantial portion of the user's forehead when the user is wearing the HMD. The elongated horizontal shape of the deformable pad 525 can be predetermined to cover a maximum amount of veins/vessels in the forehead. In some examples, the deformable pad 525 can be centered on the facial interface 512, and therefore positioned to contact a center of the user's forehead. However, other positioned are also possible. In some examples, the deformable pad 525 is off-center from the center or middle of the facial interface 512. In some examples, the facial interface 512 wraps partially around the user's head, such that the deformable pad 525 can be positioned proximate a temple of the user when the HMD is donned.

Figure 5B:
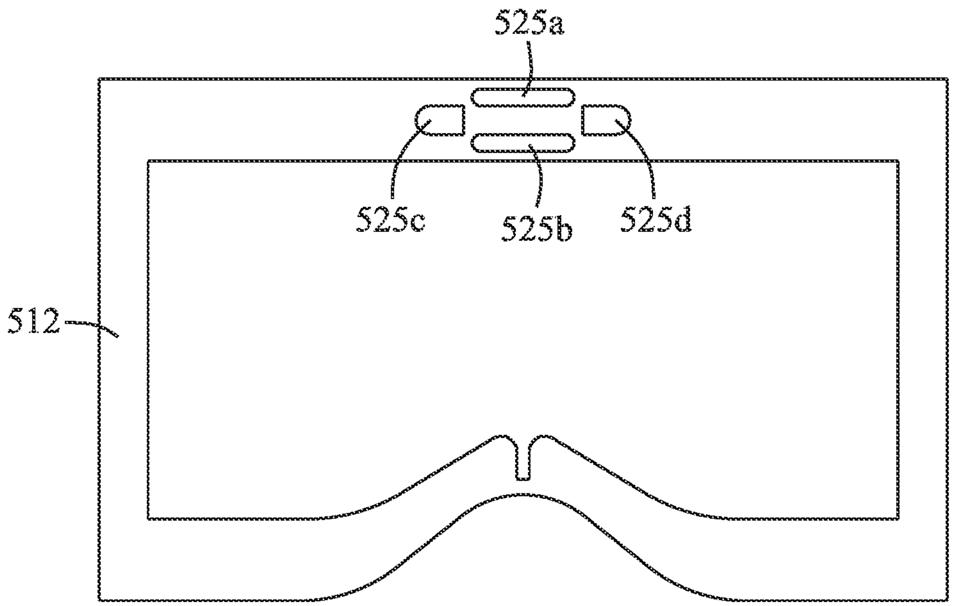
FIG. 5B shows sensors disposed on a forehead region of a facial interface of a head-mountable device.

FIG. 5B shows a rear view of the facial interface 512 having a plurality of deformable pads **525*a*, 525*b*, 525*c*, 525*d* (collectively "525"). The deformable pad 525 can each deflect to cause a change in pressure. In some examples, the facial interface 512 includes a plurality of pressure chambers. The pressure chambers can be isolated and distinct or can be in fluid communication with each other. The pressure within the channel(s) can be equalized. In some examples, each deformable pad 525** can be fluidically connected to a single sensor.

In some examples, the system include multiple sensors, each of which is fluidically connected to one or more of the deformable pads 525. The increased number of deformable pads 525 can increase accuracy and sensitivity for a head-mountable device used in combination with the facial interface 512. In some examples, a combination of the deformable pads 525 can be used to detect or track motions along the user's forehead. For example, by using at least pad **525*a* and pad 525*b*, a vertical signal or input can be monitored or tracked across the user's forehead. Likewise, using at least pad 525*c* and pad 525*d***, a horizontal signal or input can be tracked as it traverses horizontally across a user's forehead.

In some examples, the combination of pads 525 can detect a user's pulse transit time (e.g., the time it takes a pulse wave to travel between two pulse sites). For example, deformable pad **525*a* and deformable pad 525*b* can be placed over the supratrochlear artery (e.g. the arterial supply to the forehead and the anterior part of the scalp) measuring the pulse transit time from deformable pad 525*a* to deformable pad 525*b***. Similarly, any artery or combination thereof can be used to measure arterial functions, such as pulse transit times in a vertical, horizontal, or combinatory manner.

Any of the features, components, and/or parts, including the arrangements and configurations thereof shown in FIGS. 5A-5B can be included, either alone or in any combination, in any of the other examples of devices, features, components, and parts shown in the other figures described herein. Likewise, any of the features, components, and/or parts, including the arrangements and configurations thereof shown and described with reference to the other figures, can be included, either alone or in any combination, in the example of the devices, features, components, and parts shown in FIGS. 5A-5B.

Figure 6:
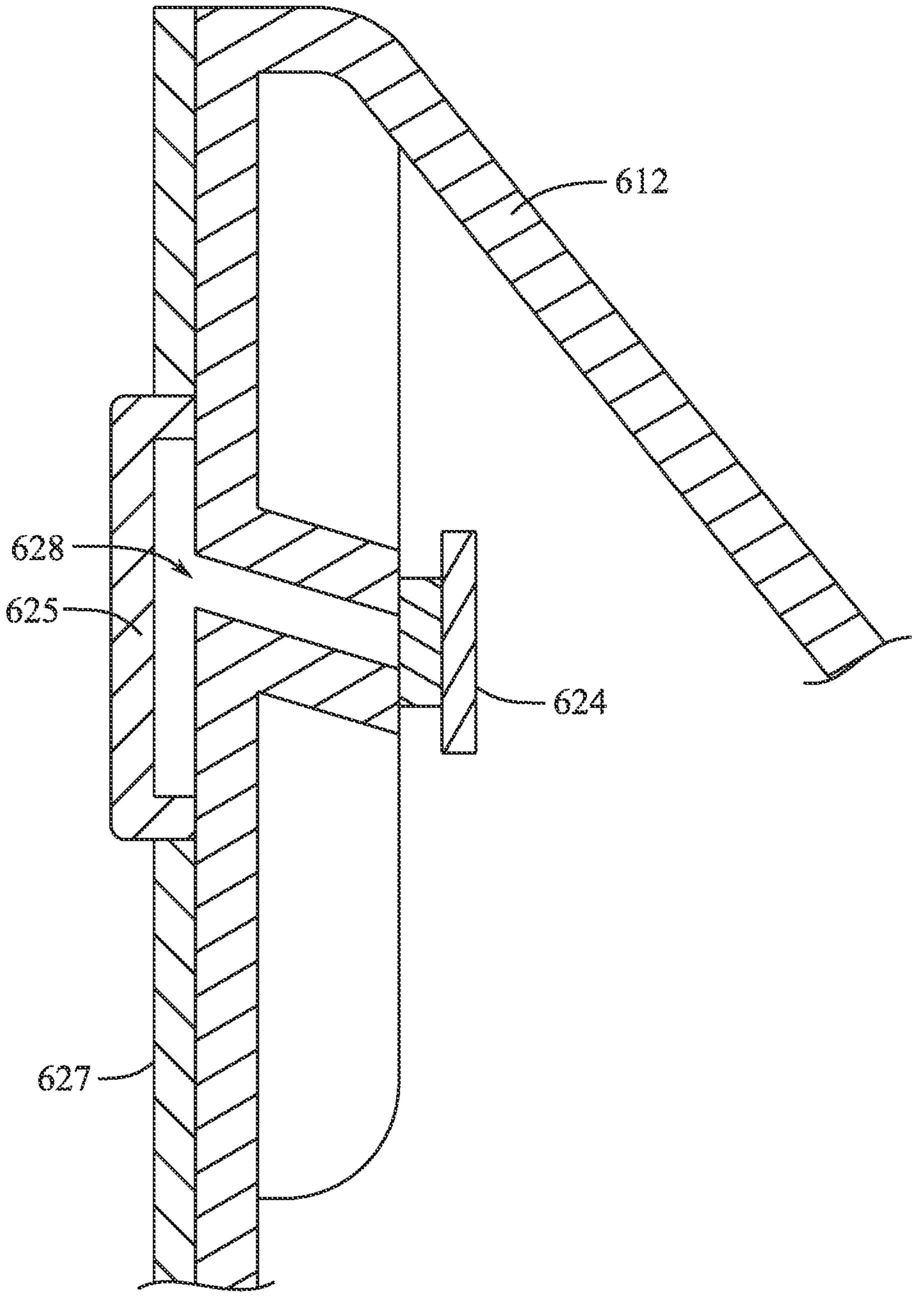
FIG. 6 shows a cross-sectional view of a pressure sensors assembly of a head-mountable device.

FIG. 6 illustrates a side cross-sectional view of a portion of a sensor module of a facial interface 612. The facial interface 612 can be substantially similar to, and can include some or all of the features of, the facial interfaces described herein, such as facial interface 112, 212, 312, 412, and 512. The sensor module of FIG. 6 includes a deformable pad 625, a contact portion 627 configured to contact a user's head, and a sensor 624.

A channel 628 can define an internal volume that places the deformable pad 625 and the sensor 624 in fluid communication. In some examples, the deformable pad can deform in response to facial movements. The deformable pad 625 can be constructed of a compressible elastomer. The facial interface can include an overmolded portion 627. The overmolded portion 627 can contact a user's face and can provide a comfortable point of contact to the user's forehead, nose, around the user's eyes, and other contact regions the overmolded portion contacts the user's face.

In some examples, the overmolded portion 627 is formed of a soft elastomer resilient to sweat/perspiration from a user. As illustrated, a pressure-based MEMS sensor 624 can be embedded or housed within the facial interface 612. The MEMS sensor can have dimension of approximately 2 mm by 2 mm. FIG. 6 illustrates the deformable pad 625 being proud from (extending or protruding from) the facial interface 612. However, in some examples, the deformable pad 625 can be flush with the facial interface 612, specifically flush with the section of the facial interface 612 that abuts or contact the forehead of the user.

An example operation of the sensor module can occur when a user, wearing the HMD, has facial movement. A facial movement can include movement in the nose, forehead, cheeks, or any other portion of the face/head. Facial movements can be indicative of respiration, pulse, and facial expressions. Because the deformable pad 625 is in close proximity or touching the user, the facial movement can push or deflect the deformable pad 625 a certain amount.

The deflection of the deformable pad 625 causes a temporary increase in the pressure within the channel 628. The change in pressure can be detected by the sensor 624, which transmits a signal, based on the pressure fluctuation to be processed (e.g., by a processor on board the HMD). In some examples, the sensor 624 can be integrated into other components of the HMD (e.g., integrated onto the headband of the HMD).

Any of the features, components, and/or parts, including the arrangements and configurations thereof shown in FIG. 6 can be included, either alone or in any combination, in any of the other examples of devices, features, components, and parts shown in the other figures described herein. Likewise, any of the features, components, and/or parts, including the arrangements and configurations thereof shown and described with reference to the other figures can be included, either alone or in any combination, in the example of the devices, features, components, and parts shown in FIG. 6.

To the extent the present exemplary systems and methods use personally identifiable information, such use of personally identifiable information should follow privacy policies and practices that are generally recognized as meeting or exceeding industry or governmental requirements for maintaining the privacy of users. In particular, personally identifiable information data should be managed and handled so as to minimize risks of unintentional or unauthorized access or use, and the nature of authorized use should be clearly indicated to users.

The foregoing description used specific, though exemplary, nomenclature to provide a thorough understanding of the described embodiments. The specific details are not required in order to practice the described examples. Thus, the foregoing descriptions of the specific embodiments and examples described herein are presented for purposes of illustration and description only, and are not intended to be exhaustive or to limit the embodiments to the precise forms disclosed. Many modifications and variations are possible in view of the above teachings.

What is claimed is:

1. A head-mountable device, comprising:
a display;
a facial interface attached to the display;
a controller;
a deformable pad positioned to contact a nasal region;
a channel defining an internal volume; and
a pressure sensor in fluid communication with the deformable pad through the internal volume, wherein the controller transmits a signal to the display based on sensor data from the pressure sensor.

2. The head-mountable device of claim 1, wherein:
the channel fluidically connects the deformable pad and the pressure sensor;
the internal volume comprises an internal pressure;
the deformable pad deflects in response to a movement of a face;
the internal pressure of the channel changes in response to the deflection; and
the pressure sensor detects the change in the internal pressure.

3. The head-mountable device of claim 1, wherein the pressure sensor is disposed within the facial interface.

4. The head-mountable device of claim 1, wherein the pressure sensor is a first pressure sensor, the head-mountable device further comprising a second pressure sensor positioned to contact a forehead of a user when the head-mountable device is worn.

5. The head-mountable device of claim 1, wherein the pressure sensor is configured to detect a movement of a user's skin.

6. The head-mountable device of claim 1, wherein the pressure sensor is configured to detect a respiration of a user.

7. The head-mountable device of claim 1, wherein the pressure sensor is configured to detect a facial expression of a user.

8. The head-mountable device of claim 1, wherein the facial interface is a first facial interface, the first facial interface being interchangeable with a second facial interface on the head-mountable device.

9. The head-mountable device of claim 8, wherein the pressure sensor is a first pressure sensor, and wherein the second facial interface comprises a second pressure sensor, different than the first pressure sensor.

10. A facial interface for a wearable device, the facial interface comprising:
a housing defining an internal volume;
a pressure sensor positioned in the internal volume; and
a membrane configured to move in response to facial movements, the membrane comprising:
a first surface configured to contact a face of a user when the facial interface is being worn; and
a second surface in fluid communication with the pressure sensor;
wherein the membrane is positionally adjustable relative to the housing; and
wherein the pressure sensor is configured to transmit an output to a controller, the controller transmitting a signal to a display to cause a change in the wearable device.

11. The facial interface of claim 10, wherein the membrane comprises a deformable elastomer.

12. The facial interface of claim 10, wherein a pressure in the internal volume changes based on movement of the membrane, the change in pressure being detectable by the pressure sensor.

13. The facial interface of claim 10, wherein a stiffness of the membrane is adjustable.

14. The facial interface of claim 10, wherein the pressure sensor has a sensitivity of about 2.5 millibar.

15. A wearable electronic device, comprising:

a display;

a facial interface positioned between the display and a face of a user when the wearable electronic device is worn by the user;

an inflatable member configured to deform in response to facial movements; and a pressure sensor configured to:

detect a deformation in the inflatable member; and transmit a first signal to a processor, the first signal based on the deformation in the inflatable member, wherein the processor sends a second signal to the display based on the first signal received from the pressure sensor.

16. The wearable electronic device of claim 15, wherein the sensor and the inflatable member are in fluid communication.

17. The wearable electronic device of claim 15, wherein the sensor comprises a pressure-based micro-electro mechanical system (MEMS) sensor.

18. The wearable electronic device of claim 15, wherein the facial interface defines a channel that fluidically couples the sensor and the inflatable member.

19. The wearable electronic device of claim 15, wherein the inflatable member removably couples to the facial interface, forming a sealed connection.

20. The wearable electronic device of claim 15, wherein the processor causes the wearable electronic device to perform an action based on the signal.

* * * * *